United States Patent
Biehl et al.

(10) Patent No.: US 10,093,681 B2
(45) Date of Patent: Oct. 9, 2018

(54) COMPOUNDS AND DERIVATIVES OF 2H-PYRIDO (3,2-B)(1, 4) OXAZIN 3)4H)-ONES AS RAF KINASE AND LRRK2 INHIBITORS

(71) Applicant: Southern Methodist University, Dallas, TX (US)

(72) Inventors: Edward R. Biehl, Dallas, TX (US); Haribabu Ankati, Dallas, TX (US); Sukanta Kamila, Coleraine (IE)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 15/273,904

(22) Filed: Sep. 23, 2016

(65) Prior Publication Data
US 2017/0008907 A1    Jan. 12, 2017

Related U.S. Application Data

(63) Continuation of application No. 13/428,023, filed on Mar. 23, 2012, now Pat. No. 9,493,452.

(60) Provisional application No. 61/467,274, filed on Mar. 24, 2011.

(51) Int. Cl.
*C07D 498/04* (2006.01)
*C07D 471/04* (2006.01)

(52) U.S. Cl.
CPC ......... *C07D 498/04* (2013.01); *C07D 471/04* (2013.01)

(58) Field of Classification Search
CPC .................................................. C07D 471/04
USPC ........................................................ 546/113
See application file for complete search history.

(56) References Cited

U.S. PATENT DOCUMENTS

| | | | |
|---|---|---|---|
| 3,759,912 A | 9/1973 | Derungs | |
| 5,116,855 A | 5/1992 | Hitoshi et al. | |
| 5,696,117 A | 12/1997 | Frechette et al. | |
| 5,707,990 A | 1/1998 | Frechette et al. | |
| 6,713,629 B2 | 3/2004 | Iwataki et al. | |
| 6,849,641 B1 * | 2/2005 | Tang ................... | C07D 209/34 514/300 |
| 7,393,869 B2 | 7/2008 | Zhang et al. | |
| 7,872,027 B2 | 1/2011 | Metallo et al. | |
| 2009/0286797 A1 | 11/2009 | Peters et al. | |
| 2012/0245347 A1 | 9/2012 | Biehl et al. | |
| 2012/0245352 A1 | 9/2012 | Biehl et al. | |
| 2013/0253021 A1 | 9/2013 | Biehl et al. | |
| 2014/0135494 A1 | 5/2014 | Biehl et al. | |

FOREIGN PATENT DOCUMENTS

| | | | |
|---|---|---|---|
| CN | 1365972 A | 8/2002 | |
| KR | 1020110137939 A | 12/2011 | |
| WO | 199616964 A1 | 6/1996 | |
| WO | WO 9616964 A1 * | 6/1996 | .......... C07D 471/04 |
| WO | 199921859 A1 | 5/1999 | |
| WO | WO 9921859 A1 * | 5/1999 | .......... C07D 471/04 |
| WO | 2010044924 A1 | 4/2010 | |
| WO | 2013142831 A1 | 9/2013 | |

OTHER PUBLICATIONS

Finch et al. Journal of Organic Chemistry (1972), 37(1), 51-4.*
Andreichikov, et al. [(Aroylpyruvoyl)amino]benzonitriles and 3-phenacylidene-6(7)-cyano-3,4-dihydro-2-quinoxalinones, 1989, Khimiko-Famiatsevticheskii Zhurnal, 23 (8), 946-949.
Balderamos, M., et al., "Synthesis and Structure-Activity Relationship Studies of 3-Substituted Indolin-2-ones as Effective Neuroprotective Agents," the Society for Experimental Biology and Medicine, Jul. 9, 2008, pp. 1395-1402.
Cutshall, N., et al., "Rhodanine Derivatives as Inhibitors of JSP-1," Bioorganic & Medicinal Chemistry Letters, vol. 15, May 2, 2005, pp. 3374-3379.
Kamila, S., et al., "An efficient microwave assisted synthesis of novel class of Rhodanine derivatives as potential HIV-1 and JSP-1 Inhibitors," Tetrahedron Letters, 2011, vol. 52, pp. 4375-4377.
Mamedov, Vakhid, A., et al, "Efficient synthesis of 2-(pyrazol-e-yl)benzimidazoles from 3-arylacylidene-3,4-dihydroquinoxalin-2(1H)-ones and hydrazine and hydrate via a novel arrangement," Tetrahedron Letters 50, 2009, 5186-5189.
Korean Intellectual Property Office (ISA) International Search Report and Written Opinion for PCT/US2013/033584 dated Jul. 18, 2013.
Ramkumar, K., et al, "Design, synthesis and structure-activity studies of rhodanine derivatives as HIV-1 integrase inhibitors," Molecules, 2010, vol. 15, pp. 39-58-3992.
Rinaldi, M., et al. "A versatile and practical synthesis toward the development of novel HIVE-1 integrase inhibitors,", Chem. Med. Chem., 2011, vol. 6, pp. 343-352.
Sierra-Aragon, S., et al., "Targets for Inhibition of HIV Replication: Entry, Enzyme Action, Release and Maturation," Basic Principles of HIV, vol. 55, Jan. 24, 2012, pp. 84-97.
Xia, Min, et al, "Sulfamic Acid as an Effective Catalyst in Solvent-Free Synthesis of β-Enaminoketone Derivatives and X-ray Crystallography of Their Representatives," Synthetic Communications, 2008, 38:1268-1278.
Machine Translation of Publication of KR 20110137939 Dec. 26, 2011.

* cited by examiner

*Primary Examiner* — Kahsay Habte
(74) *Attorney, Agent, or Firm* — Edwin S. Flores; Chalker Flores, LLP

(57) ABSTRACT

The present invention provides oxazine compounds, method of using and method of making oxazine compounds and its pharmaceutical use.

1 Claim, No Drawings

COMPOUNDS AND DERIVATIVES OF 2H-PYRIDO (3,2-B)(1, 4) OXAZIN 3)4H)-ONES AS RAF KINASE AND LRRK2 INHIBITORS

CROSS-REFERENCE TO RELATED APPLICATIONS

This patent application is a continuation of U.S. patent application Ser. No. 13/428,023 filed on Mar. 23, 2012, which is a non-provisional patent application of U.S. provisional patent application 61/467,274 filed on Mar. 24, 2011 and entitled "Compounds and Derivatives of 2H-Pyrido (3,2-b)(1,4) Oxazin 3)4H)-ones as raf Kinase and LRRK2 Inhibitors", which are hereby incorporated by reference in their entirety.

STATEMENT OF FEDERALLY FUNDED RESEARCH

Not Applicable.

SEQUENCE LISTING

Not Applicable.

INCORPORATION-BY-REFERENCE OF MATERIALS FILED ON COMPACT DISC

Not Applicable.

TECHNICAL FIELD OF THE INVENTION

The present invention relates in general to the field of pharmaceutical compositions and synthesis, and more particularly, to novel compositions and methods for preparing the compound and its pharmaceutical use.

BACKGROUND OF THE INVENTION

U.S. Pat. No. 5,696,117 entitled, Benzoxazine antimicrobial Agents, discloses benzoxazine and pyrido-oxazine antibacterial compounds, pharmaceutical compositions containing the compounds, and methods for their production and use. These compounds are effective in inhibiting the action of a bacterial histidine protein kinase and are thus useful as anti-infective agents against a variety of bacterial organisms, including organisms which are resistant to other known antibiotics.

U.S. Pat. No. 5,707,990 entitled, 2-substituted amino and thio alkyl benzoxazine antimicrobial agents discloses benzoxazine and pyrido-oxazine antibacterial compounds with a fused phenyl or fused pyridyl moiety and a substituted amine or substituted thio moiety as herein described, pharmaceutical compositions containing the compounds, methods for their production and their use in treating bacterial infections.

BRIEF SUMMARY OF THE INVENTION

One embodiment of the present invention provides a compound of formula or pharmaceutical salts thereof:

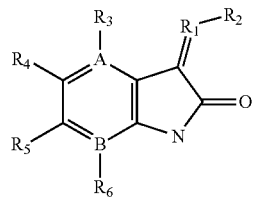

wherein A and B are individually an C, O, N or S and R1 is an alkyl or an alkenyl and R2 is a phenyl, benzyloxyl, pyridyl, indolone, pyrrol, carbamoyl, pyridine, substituted phenyl, substituted benzyloxyl, substituted pyridine, or substituted pyridyl and R3-R6 are individually a hydrogen, an amine or a halogen.

One embodiment of the present invention also provides a compound of formula or pharmaceutical salts thereof:

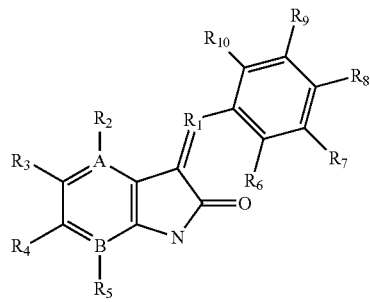

wherein A and B are individually an C, O, N or S and R1 is an alkyl or an alkenyl and R2 is a phenyl, benzyloxyl, pyridyl, indolone, pyrrol, carbamoyl, pyridine, substituted phenyl, substituted benzyloxyl, substituted pyridine, or substituted pyridyl and R3 is a hydrogen or a halogen. In some embodiments, A is a C, B is a N and R1 is a CH and in other embodiments $R_1$-$R_{10}$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group.

One embodiment of the present invention provides a compound of formula or pharmaceutical salts thereof:

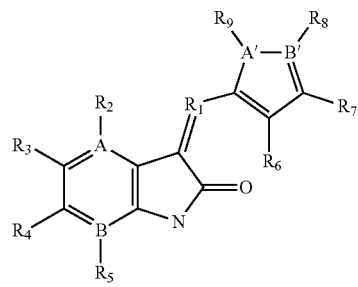

wherein A, A', B and B' are individually an C, O, N or S and R1 is an alkyl or an alkenyl and R2 is a phenyl, benzyloxyl, pyridyl, indolone, pyrrol, carbamoyl, pyridine, substituted phenyl, substituted benzyloxyl, substituted pyridine, or substituted pyridyl and R3 is a hydrogen or a halogen. In some embodiments, A and B' are C, R1 is a CH, and B and A' are N and in other embodiments $R_1$-$R_{10}$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group.

One embodiment of the present invention provides a compound of formula or pharmaceutical salts thereof:

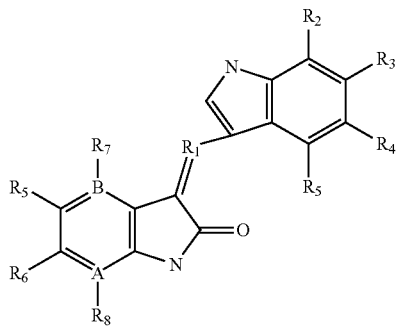

wherein A and B are individually an C, O, N or S and $R_1$-$R_8$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. In some embodiments, A is a C, R1 is a CH, and B is a N or A is a N, R1 is a CH, and B is a C.

One embodiment of the present invention provides a compound of formula or pharmaceutical salts thereof:

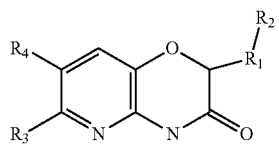

wherein R1 is an alkyl or an alkenyl and R2 is a phenyl, benzyloxyl, pyridyl, indolone, pyrrol, carbamoyl, pyridine, substituted phenyl, substituted benzyloxyl, substituted pyridine, or substituted pyridyl, and R3 and R4 are independently a hydrogen, a halogen, an alkyl or an alkenyl.

One embodiment of the present invention provides a compound of formula or pharmaceutical salts thereof:

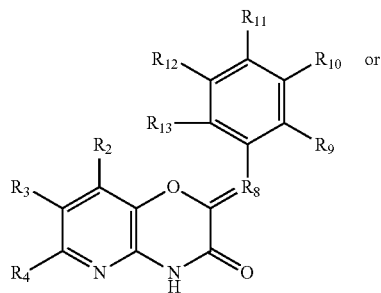

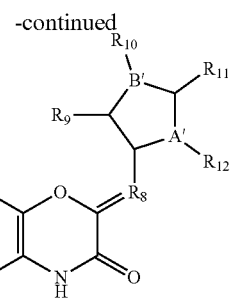

wherein A', and B' are selected from C, N, S, O. $R_2$-$R_4$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{13}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "alkyl", "alkenyl", "alkynyl" and "alkylene" denotes hydrocarbon chains typically ranging from about 1 to about 12 carbon atoms in length, preferably 1 to about 6 atoms, and includes straight and branched chains. Unless otherwise noted, the preferred embodiment of any alkyl or alkylene referred to herein is C1-C6 alkyl (e.g., methyl or ethyl).

The term "cycloalkyl" denotes a saturated or unsaturated cyclic hydrocarbon chain, including bridged, fused, or spiro cyclic compounds, preferably comprising 3 to about 12 carbon atoms, more preferably 3 to about 8.

The term "aryl" denotes one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

The term "heteroaryl" denotes an aryl group containing from one to four heteroatoms, preferably N, O, or S, or a combination thereof, which heteroaryl group is optionally substituted at carbon or nitrogen atom(s) with C1-C6 alkyl, —CF3, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

The term "heterocycle" or "heterocyclic" denotes one or more rings of 5-12 atoms, preferably 5-7 atoms, with or without unsaturation or aromatic character and at least one ring atom which is not carbon. Preferred heteroatoms include sulfur, oxygen, and nitrogen. Multiple rings may be fused.

The term "heteroatom" denotes any non-carbon atom in a hydrocarbon analog compound. Examples include oxygen, sulfur, nitrogen, phosphorus, arsenic, silicon, selenium, tellurium, tin, and boron.

The term "alkylene" denotes a divalent alkyl group as defined above, such as methylene (—CH$_2$—), propylene (—CH$_2$ CH$_2$ CH$_2$—), chloroethylene (—CHClCH$_2$—), 2-thiobutene —CH$_2$ CH(SH)CH$_2$ CH$_2$, 1-bromo-3-hydroxyl-4-methylpentene (—CHBrCH$_2$CH(OH)CH(CH$_3$) CH$_2$—), and the like.

The term "alkenyl" denotes branched or unbranched hydrocarbon chains containing one or more carbon-carbon double bonds.

The term "alkynyl" denotes branched or unbranched hydrocarbon chains containing one or more carbon-carbon triple bonds.

The term "aryl" denotes a chain of carbon atoms which form at least one aromatic ring having preferably between about 6-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl.

The term "amido" denotes an amide linkage: —C(O)NHR (wherein R is hydrogen or alkyl).

The term "amino" denotes an amine linkage: —NR—, wherein R is hydrogen or alkyl. The term "carboxyl" denotes —C(O)O—, and the term "carbonyl" denotes —C(O)—.

The term "alkylcarboxyl" denote an alkyl group as defined above substituted with a C(O)O group, for example, CH$_3$C(O)O—, CH$_3$CH$_2$C(O)O—, etc.

The term "carbocycle" denotes cyclic hydrocarbon chain having about 5 to about 8 ring carbons such as cyclopentyl, cylcohexyl, etc. These groups can be optionally substituted with one or more functional groups as defined under "alkyl" above.

The term "halogen" includes chlorine, fluorine, bromine, iodine and mixtures thereof The term "heterocycle" denotes straight chain or ring system that may contain from zero to four heteroatoms selected from N, O, and S, wherein the nitrogen and sulfur atoms are optionally oxidized, and the nitrogen atom(s) are optionally quaternized.

The term "carbamoyl" denotes the group —C(O)NH$_2$.

The term "hydroxyalkyl" denotes an alkyl group as defined above which is substituted by a hydroxy group.

The term "alkylcarbonyl", alone or in combination, means an acyl group derived from an alkanecarboxylic acid, i.e. alkyl-C(O)—, such as acetyl, propionyl, butyryl, valeryl, 4-methylvaleryl etc.

One embodiment of the present invention provides compound of the general formula:

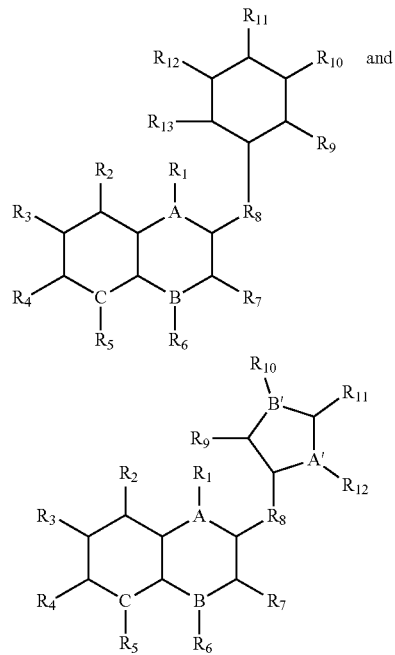

wherein A, A', B, B' and C are selected from C, N, S, O. $R_1$-$R_7$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{13}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

One embodiment of the present invention provides compound of the general formula:

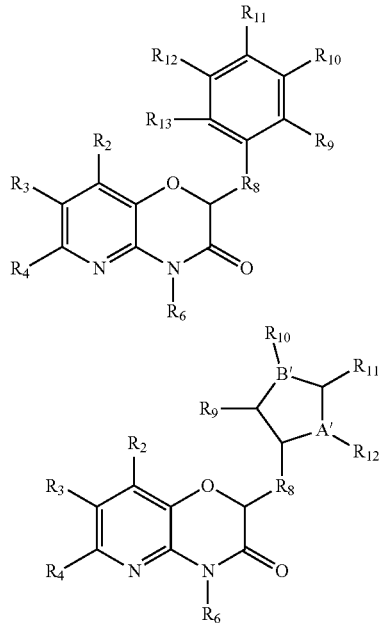

and wherein A', and B' are selected from C, N, S, O. $R_2$-$R_6$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{13}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

One embodiment of the present invention provides compound of the general formula:

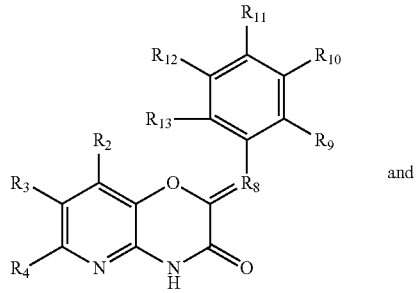

and

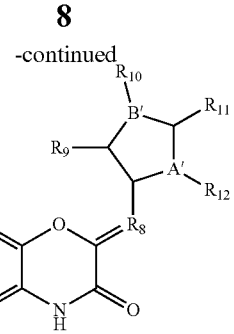

wherein A', and B' are selected from C, N, S, O. $R_2$-$R_4$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{13}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

One embodiment of the present invention provides compound of the general formula:

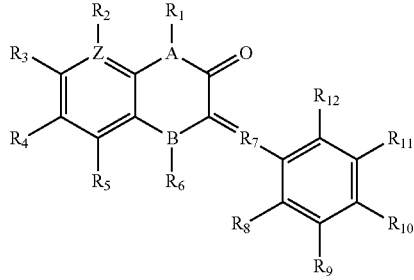

For example, in the formula above A is a N; B is a O; Z is a N; $R_1$, $R_3$, $R_4$, $R_5$, $R_8$, and $R_{12}$ are a H; $R_2$ and $R_6$ are not present; $R_7$ is a C; $R_9$ and $R_{11}$ are Br; and $R_7$ is a OAc. For example, in the formula above A is a N; B is a O; Z is a N; $R_1$, $R_3$, $R_4$, $R_5$, $R_8$, and $R_{12}$ are a H; $R_2$ and $R_6$ are not present; $R_7$ is a C; $R_9$ and $R_{11}$ are H; and $R_7$ is a $N(CH_3)_2$. For example, in the formula above A is a N; B is a O; Z is a N; $R_1$, $R_3$, $R_4$, $R_5$, $R_8$, and $R_{12}$ are a H; $R_2$ and $R_6$ are not present; $R_7$ is a C; and $R_9$, $R_7$ and $R_{11}$ are OMe. For example, in the formula above A is a N; B is a O; Z is a N; $R_1$, $R_3$, $R_4$, $R_5$, $R_8$, and $R_{12}$ are a H; $R_2$ and $R_6$ are not present; $R_7$ is a C; $R_9$ and $R_{11}$ are Br; and $R_7$ is a H. For example, in the formula above A is a N; B is a O; Z is a N; $R_1$, $R_3$, $R_4$, $R_5$, $R_8$, and $R_{12}$ are a H; $R_2$ and $R_6$ are not present; $R_7$ is a C; $R_9$ and $R_{11}$ are Br; and $R_7$ is a OH. For example, in the formula above A is a N; B is a O; Z is a N; $R_1$, $R_4$, $R_5$, $R_8$, and $R_{12}$ are a H; $R_2$ and $R_6$ are not present; $R_7$ is a C; $R_3$ is a Cl; $R_9$ and $R_{11}$ are Br; and $R_7$ is a OAc. For example, in the formula above A is a N; B is a O; Z is a N; $R_1$, $R_4$, $R_5$, $R_8$, and $R_{12}$ are a H; $R_2$ and $R_6$ are not present; $R_7$ is a C; $R_3$ is a $CH_3$; $R_9$ and $R_{11}$ are Br; and $R_7$ is a OAc. For example, in the formula above A is a N; B is a O and Z is a N; $R_1$, $R_3$, $R_4$, $R_5$, $R_8$, and $R_{12}$ are a H; $R_2$ and $R_6$ are not present; $R_7$ is a C; $R_9$ and $R_{11}$ are Br; and $R_7$ is a OAc.

For example,
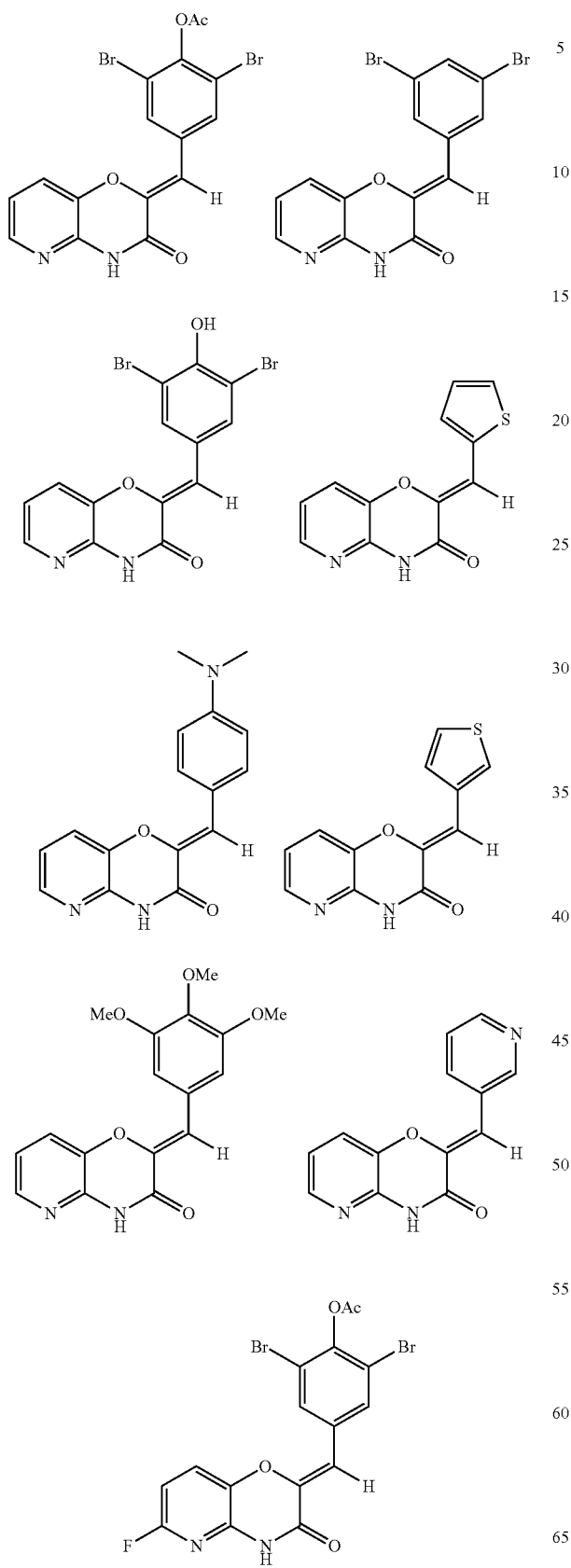
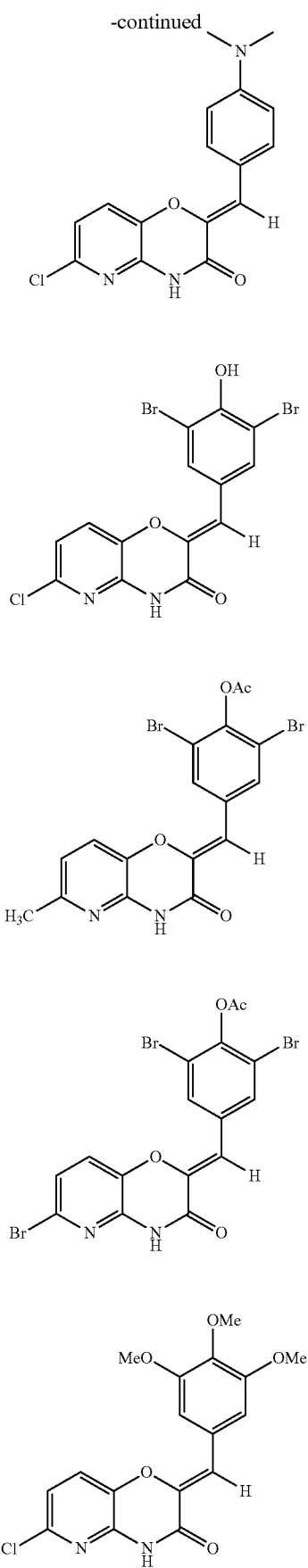

-continued

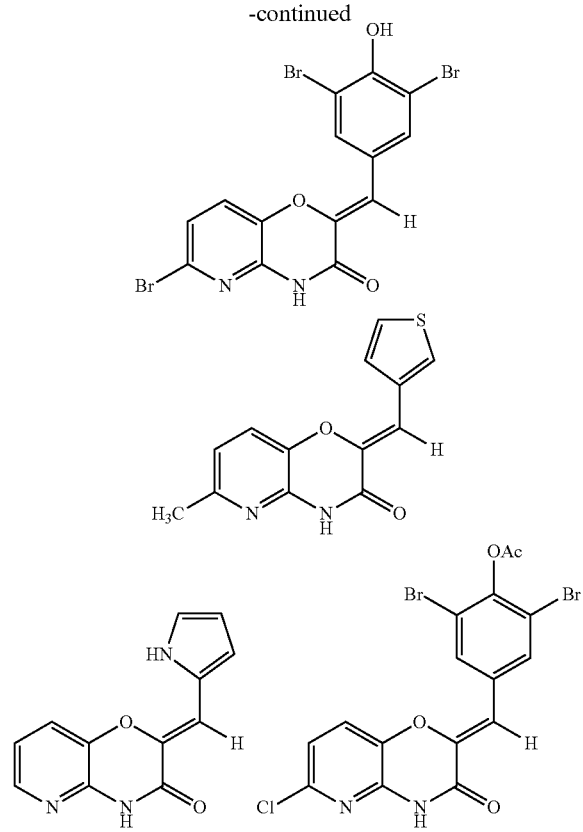

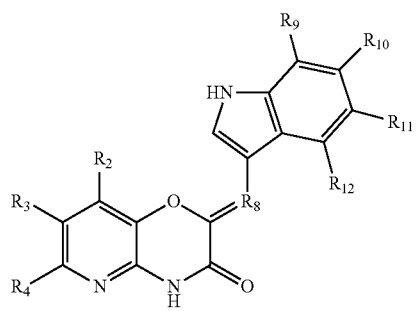

One embodiment of the present invention provides compound of the general formula:

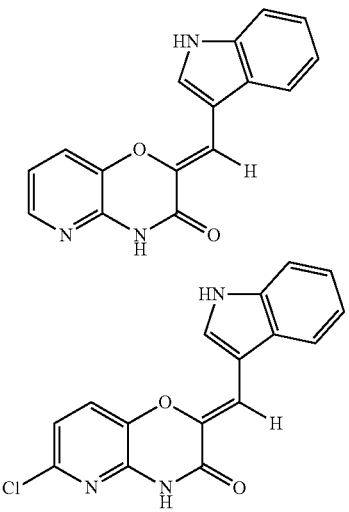

wherein $R_2$-$R_4$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{12}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

For example,

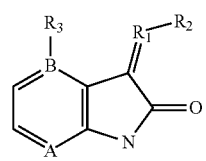

A compound of formula or pharmaceutical salts thereof:

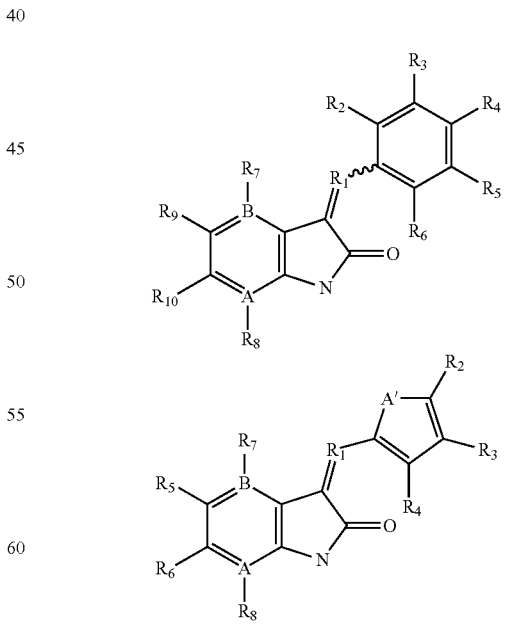

wherein A and B are individually an C, O, N or S and R1 is an alkyl or an alkenyl and R2 is a phenyl, benzyloxyl, pyridyl, indolone, pyrrol, carbamoyl, pyridine, substituted phenyl, substituted benzyloxyl, substituted pyridine, or substituted pyridyl and R3 is a hydrogen, a halogen, an amino, an alkyl or an alkenyl.

A compound of formula or pharmaceutical salts thereof:

wherein A and B are individually an C, O, N or S and $R_1$-$R_{10}$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. For example,
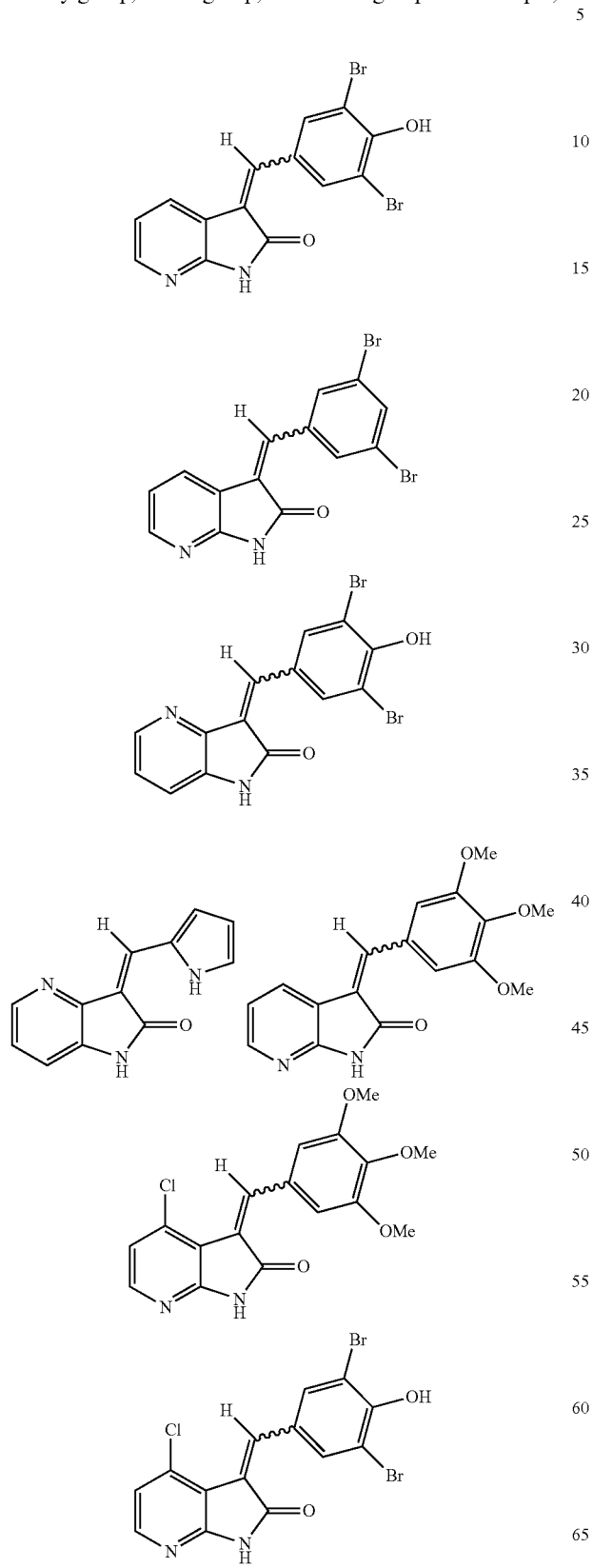
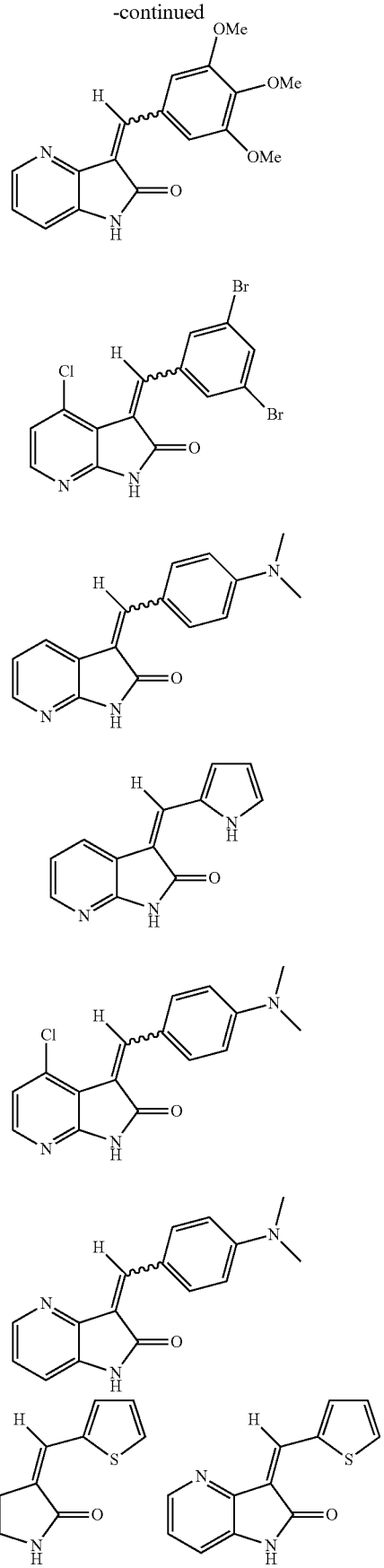

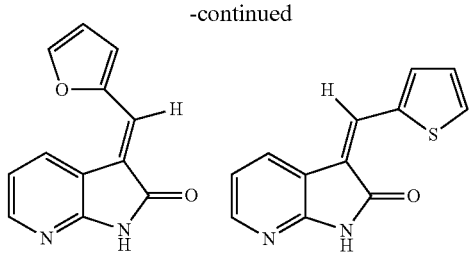

A compound of formula or pharmaceutical salts thereof:

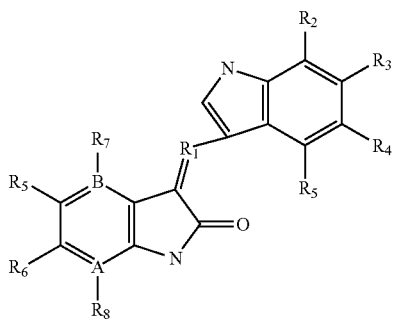

wherein A and B are individually an C, O, N or S and $R_1$-$R_8$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. For example:

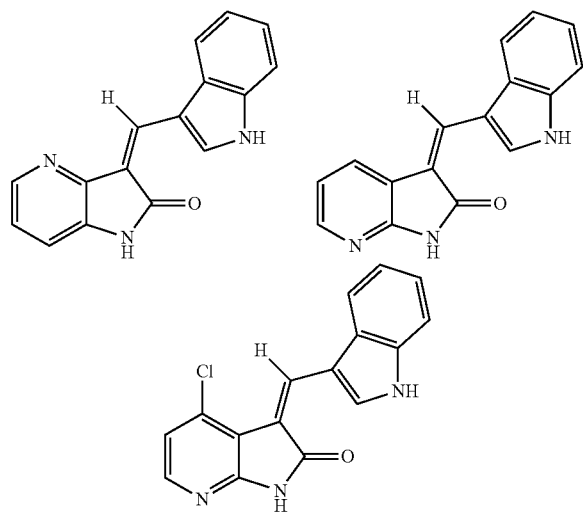

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A compound selected from 3-(3,5-dibromo-4-hydroxybenzylidene)-1H-pyrrolo[2,3-b]pyridin-2(3H)-one; 3-(3,5-dibromobenzylidene)-1H-pyrrolo[2,3-b]pyridin-2(3H)-one; 3-(3,5-dibromo-4-hydroxybenzylidene)-1H-pyrrolo[3,2-b]pyridin-2(3H)-one; 3-(3,4,5-trimethoxybenzylidene)-1H-pyrrolo[2,3-b]pyridin-2(3H)-one; 4-chloro-3-(3,5-dibromobenzylidene)-1H-pyrrolo[2,3-b]pyridin-2(3H)-one; (Z)-3-(1H-pyrrol-2-yl)methylene)-1H-pyrrolo[2,3-b]pyridin-2(3H)-one; (Z)-3-(1H-pyrrol-2-yl)methylene)-1H-pyrrolo[3,2-b]pyridin-2(3H)-one; 4-chloro-3-(3,4,5-trimethoxybenzylidene)-1H-pyrrolo[2,3-b]pyridin-2(3H)-one; 3-(3,4,5-trimethoxybenzylidene)-1H-pyrrolo[3,2-b]pyridin-2(3H)-one; 3-(4-(dimethylamino)benzylidene)-1H-pyrrolo[2,3-b]pyridin-2(3H)-one; 4-chloro-3-(4-(dimethylamino)benzylidene)-1H-pyrrolo[2,3-b]pyridin-2(3H)-one; 3-(4-(dimethylamino)benzylidene)-1H-pyrrolo[3,2-b]pyridin-2(3H)-one; (Z)-3-(1H-indol-3-yl)methylene)-1H-pyrrolo[3,2-b]pyridin-2(3H)-one; (Z)-3-(1H-indol-3-yl)methylene)-1H-pyrrolo[2,3-b]pyridin-2(3H)-one; (Z)-3-(1H-indol-3-yl)methylene)-4-chloro-1H-pyrrolo[2,3-b]pyridin-2(3H)-one; (Z)-3-(thiophen-2-ylmethylene)-1H-pyrrolo[3,2-b]pyridin-2(3H)-one; (Z)-3-(thiophen-2-ylmethylene)-1H-pyrrolo[2,3-b]pyridin-2(3H)-one; (Z)-4-chloro-3-(thiophen-2-ylmethylene)-1H-pyrrolo[2,3-b]pyridin-2(3H)-one; and (E)-3-(furan-2-ylmethylene)-1H-pyrrolo[2,3-b]pyridin-2(3H)-one.

\* \* \* \* \*